(12) United States Patent
Hansson

(10) Patent No.: US 6,474,991 B1
(45) Date of Patent: *Nov. 5, 2002

(54) IMPLANT SYSTEM

(75) Inventor: Stig Hansson, Mölndal (SE)

(73) Assignee: Astra Aktiebolag, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,111

(22) PCT Filed: Apr. 21, 1998

(86) PCT No.: PCT/SE98/00729
§ 371 (c)(1),
(2), (4) Date: May 21, 1998

(87) PCT Pub. No.: WO98/48728
PCT Pub. Date: Nov. 5, 1998

(30) Foreign Application Priority Data

Apr. 28, 1997 (SE) .............................. 9701581

(51) Int. Cl.[7] .................................. A61C 8/00
(52) U.S. Cl. ...................... 433/173; 433/174
(58) Field of Search ................. 433/173, 174

(56) References Cited

U.S. PATENT DOCUMENTS

| | | | | |
|---|---|---|---|---|
| 4,713,006 A | * | 12/1987 | Hakamatsuka et al. | 433/173 |
| 4,758,160 A | * | 7/1988 | Ismail | 433/173 |
| 5,092,771 A | * | 3/1992 | Tatum, III | 433/173 |
| 5,110,292 A | * | 5/1992 | Balfour et al. | 433/173 |
| 5,114,343 A | * | 5/1992 | Musikanti et al. | 433/173 |
| 5,282,746 A | * | 2/1994 | Sellers et al. | 433/173 |
| 5,417,570 A | * | 5/1995 | Zuest et al. | 433/173 |
| 5,458,488 A | * | 10/1995 | Chaifoux | 433/173 |
| 5,695,335 A | * | 12/1997 | Haas et al. | 433/173 |

FOREIGN PATENT DOCUMENTS

| | | |
|---|---|---|
| EP | 0288445 | 4/1987 |
| WO | 8502337 | 6/1985 |

* cited by examiner

*Primary Examiner*—Ralph A. Lewis
(74) *Attorney, Agent, or Firm*—White & Case LLP

(57) ABSTRACT

A dental implant system comprising a fixture (301; 401; 501) for implantation in bone tissue (312, 314; 512, 514) of the maxilla or mandible by displacement thereof in a forward direction, the fixture having a forward end, a rearward end (330; 430; 530), and an outer surface (305; 405; 505) which extends between the forward and rearward ends and which forwardly of a predetermined position (307; 407; 507) on the outer surface is adapted for interlocking with bone tissue of the maxilla or mandible; and a superstructure (402) for mounting on the fixture, the superstructure having a forward end for interfacing with the rearward end of the fixture, the forward end of the superstructure and the rearward end of the fixture each presenting interfacing surfaces for interfacing with one another. The rearward end of the fixture and the forward end of the superstructure are so constructed and dimensioned that a predetermined interfacing surface of the superstructure (423) is able to interface in the forward direction with a predetermined interfacing surface of the fixture (311; 409; 525) which is at a level which is disposed forwardly of the predetermined position on the outer surface. A more favourable stress distribution in the bone tissue adjacent the fixture results.

35 Claims, 11 Drawing Sheets

IMPLANT SYSTEM

BACKGROUND OF THE INVENTION

The present invention relates to an implant system, specifically a dental implant system for a partially or fully edentulous patient which comprises a fixture for implantation into the bone tissue of the maxilla or mandible of the patient and a superstructure for mounting to the fixture which in turn supports or presents a dental restoration comprising one or more artificial replacement teeth. As an example, the superstructure may be an abutment which is adapted in use to be connected to the implanted fixture to bridge the soft tissue layer (gingiva) overlying the maxilla or mandible for a restoration structure such as a crown or bridge to be secured thereto.

In a typical dental implant system the superstructure is screw retained to the fixture. To this end, the fixture has an internally threaded socket which opens in a rear end of the fixture. The internal threads may be present throughout the socket or alternatively just in a is section of the socket. The superstructure is then either (i) integrally formed with an externally threaded projection for screwing into the internally threaded socket to secure the superstructure to the fixture, or (ii) comprises a sleeve part having a lumen in which a transverse bearing surface is provided, and a screw part for passage through the lumen of the sleeve into the internally threaded socket, the screw having an enlarged head which is adapted in use to bear against the transverse bearing surface in the lumen of the sleeve thereby ensuring that the superstructure is secured to the fixture on screwing of the screw into the internally threaded socket.

In other dental implant systems the superstructure is secured to the fixture through non-screw thread connections, e.g. by cementing.

Whatever the form of securement of the superstructure to the fixture, the superstructure transmits a load to the fixture in the implantation direction through mutually interfacing surfaces.

Fixation of a fixture of a dental implant system in the bone tissue of the maxilla or mandible primarily relies upon mechanical interlocking of bone tissue to the outer surface of the fixture. Substantial interlocking between the outer surface of a fixture and the bone tissue of the maxilla or mandible occurs when the outer surface is roughened, for example by providing the fixture outer surface with screw threads, recesses, holes etc. (macroroughening), forming pits in the fixture outer surface by blasting, plasma spraying, etching, hydroxyapatite coating, the provision of beads on the outer surface etc. (microroughening) or machining the fixture outer surface. Interlocking between the outer surface of a fixture and bone tissue of the maxilla or mandible into which the fixture is implanted enables the fixture to greater withstand shear stresses. One can consider this to be due to bone tissue growing into the recesses in the fixture outer surface created by the roughening.

A macroroughened fixture outer surface produces more effective interlocking than a microroughened fixture outer surface which in turn produces more effective interlocking than a machined fixture outer surface. All, however, produce more effective interlocking than fixtures having an outer surface which is smooth, e.g. a polished outer surface. More than one form of surface roughening can be applied to a fixture to promote interlocking. For example, it is known to provide a fixture with both a macro- and a microroughened outer surface.

In 1892 it was suggested by J. Wolff (*Das Gesetz der Transformation der Knochen. Berlin: A. Hirschald*, 1892) that bone tissue remodels itself in response to the mechanical loading history of the bone and in accordance with mathematical laws. This has since proved to be correct and is therefore now known as Wolff's law. Some consequences of Wolff's law are that 1. If the stresses or strains to which bone tissue is exposed are lowered a net loss of bone tissue (bone resorption) will result until a new steady state is obtained where the stresses or strains are normal.
2. If the stresses or strains to which bone tissue is exposed are normal then no net change to the bone tissue will result.
3. If the stresses or strains to which bone tissue is exposed are increased within physiological limits bone tissue build up will result until a new steady state is obtained where the stresses or strains are normal.
4. If the stresses or strains to which bone tissue is exposed are extremely high then bone resorption will result.

Wolff's law thus indicates the need for stress conditions in the bone tissue adjacent an implant fixture which are favourable for the maintenance of a steady state in the bone tissue. Otherwise, marginal bone resorption will result which will cause destabilisation of the osseointegration of the fixture with the bone tissue and a reduction in the aesthetic appeal of the dental implant system when implanted, an important commercial consideration.

With this in mind, the Applicant's have identified an interdependence between the stress conditions in the bone tissue adjacent an implant fixture and the position of the interfacing surfaces through which a fixture is loaded in the implantation direction by a superstructure vis-à-vis the level on the fixture outer surface where interlocking starts. The present invention proposes to provide a dental implant system which takes account of this interdependence to improve the stress conditions in the bone tissue adjacent the outer surface of an implanted fixture.

SUMMARY OF THE INVENTION

According to the present invention there is provided a dental implant system comprising:
  a fixture for implantation in bone tissue of the maxilla or mandible by displacement thereof in a forward direction, the fixture having:
    a forward end,
    a rearward end, and
    an outer surface which extends between the forward and rearward ends and which forwardly of a predetermined position on the outer surface is adapted for interlocking with bone tissue of the maxilla or mandible; and
  a superstructure for mounting on the fixture, the superstructure having:
    a forward end for interfacing with the rearward end of the fixture, the forward end of the superstructure and the rearward end of the fixture presenting interfacing surfaces for interfacing with one another;

characterised in that the rearward end of the fixture and the forward end of the superstructure are so constructed and dimensioned that a predetermined interfacing surface of the superstructure is able to interface in the forward direction with a predetermined interfacing surface of the fixture which is at a level which is disposed forwardly of the predetermined position on the outer surface.

The result of this arrangement is that when the fixture is implanted the superstructure applies a load to the fixture in the forward direction through interfacing surfaces at a level which is disposed forwardly of the predetermined position on the fixture outer surface which is the attachment level at which bone tissue starts to interlock with the fixture when implanted. Finite element analysis indicates that loading of a fixture in the forward direction forwardly of the attachment level results in an improved stress distribution in the adjacent bone tissue of the maxilla or mandible. For example, application of a forwardly directed load through interfacing surfaces forward of the attachment level shifts the peak interfacial shear stress forwardly where the risk of triggering off stress induced bone resorption is less. In addition, the longitudinal compressive stresses (relative to the maxilla or mandible ridge) in the bone tissue and the stresses caused by the horizontal loads or bending moments on the fixture are less as one moves more forwardly into the bone tissue and therefore the peak interfacial shear stress generated in the bone tissue can be more easily accommodated there. The peak interfacial shear stress value is also generally reduced in value.

In an embodiment of the invention the predetermined interfacing surfaces of the fixture and the superstructure are the only interfacing surfaces of the fixture and superstructure which are adapted to interface with one another in the forward direction. Thus, all of the forwardly directed load received by the fixture from the superstructure is at a level below the attachment level. Finite element analysis indicates that applying all of the forwardly directed load to the fixture forwardly of the attachment level gives the greatest improvement in the stress distribution in the adjacent bone tissue of the maxilla or mandible.

The benefit of the invention is still attained, though, where the fixture is loaded in the forward direction through interfacing surfaces forward of the attachment level and interfacing surfaces at, or rearward of, the attachment level. Accordingly, in another embodiment of the invention the predetermined interfacing surfaces of the fixture and superstructure are predetermined forward interfacing surfaces and the forward end of the superstructure and the rearward end of the fixture are so constructed and dimensioned that the forward end of the superstructure presents a predetermined rearward interfacing surface for interfacing in the forward direction with a predetermined rearward interfacing surface presented by the rearward end of the fixture at a level disposed at, or rearwardly of, the predetermined position on the fixture outer surface. In this case it is preferable that a major part of the collective forwardly directed loading applied to the fixture be at a level forward of the predetermined position on the fixture outer surface or attachment level. However, provided a forwardly directed load is applied to the fixture forwardly of the attachment level, whether this be the major part or the minor part of a forwardly directed load distributed on both sides of a level coinciding with the attachment level, an improved stress distribution will result in the bone tissue adjacent the fixture as compared to the case where all of the forwardly directed load is applied at or rearward of the attachment level, as in the prior art as will be illustrated hereinafter.

An improved stress condition in the bone tissue adjacent the fixture will be obtained even if the predetermined interfacing surface of the fixture is disposed only marginally forwardly of the predetermined position on the fixture outer surface, e.g. at a level which is approximately 0.1–1 mm forward of the predetermined position on the fixture outer surface. A greater improvement will be forthcoming, however, if the predetermined interfacing surface of the fixture is disposed well forward of the predetermined position on the fixture outer surface. Thus, preferably the fixture and superstructure are adapted in use to interface at a level which is greater than 1 mm forward of the predetermined position on the fixture outer surface, more preferably greater than 3 mm forward of the predetermined position on the fixture outer surface and even more preferably greater than 5 mm forward of the predetermined position on the fixture outer surface, e.g. approximately 10 mm forward of the predetermined position on the fixture outer surface.

In embodiments of the invention hereinafter to be described a female recess is provided in the rearward end of the fixture having a boundary wall which extends from an opening in the rearward end to a level forwardly of the predetermined position on the fixture outer surface, the predetermined interfacing surface of the fixture is a predetermined surface of the boundary wall of the female recess which is disposed forwardly of the predetermined position on the fixture outer surface, and the predetermined interfacing surface of the superstructure is a predetermined surface of a boundary wall of a male projection provided at the forward end of the superstructure.

In an embodiment of the invention the predetermined surfaces of the boundary walls of the female recess and male projection have a generally conical profile with flank surfaces which converge in the forward direction at a common angle or a substantially common angle.

In an embodiment of the invention hereinafter to be described the predetermined surfaces of the boundary walls of the male projection and female recess are presented by predetermined forward sections of the respective boundary walls and the boundary walls of the male projection and female recess each have rearward section s which extend rearwardly from the predetermined forward section and which are so constructed and dimensioned that they are spaced apart when the predetermined forward sections interface. To this end, the rearward section of the boundary wall of the female recess may be of a conical profile with flank surfaces which converge in the forward direction at the common angle or substantially the common angle and the rearward section of the male projection may be of a conical profile with flank surfaces which converge in the forward direction at an angle which is more acute relative to the forward direction than the common angle.

In an embodiment of the invention hereinafter to be described the rearward section of the boundary wall of the female recess extends rearwardly to the rearward end of the fixture.

In another embodiment of the invention hereinafter to be described the predetermined surfaces of the boundary walls of the female recess and male projection are presented by predetermined forward sections of the respective boundary walls, the predetermined rearward interfacing surface of the fixture is presented by a predetermined rearward section of the boundary wall of the female recess disposed at, or rearwardly of, the predetermined position on the fixture outer surface and the predetermined rearward interfacing surface of the superstructure is presented by a predetermined rearward section of the boundary wall of the male projection. By making the extent of the predetermined forward section of the boundary wall of the female recess in the forward direction greater than the extent of the predetermined rearward section of the boundary wall of the female recess in the forward direction the major part of the forwardly directed loading applied to the fixture by the superstructure will be applied forward of the predetermined position on the fixture outer surface.

In an embodiment of the invention the predetermined forward and rearward sections of the boundary walls of the female recess and male projection are contiguous.

In an embodiment of the invention the predetermined rearward sections of the boundary walls of the female recess and male projection have a generally conical profile with flank surfaces which converge in the forward direction at the common angle or substantially the common angle.

In an alternative embodiment of the invention hereinafter to be described the predetermined surface of the boundary wall of the female recess is presented by a transverse section of the boundary wall. The transverse section of the boundary wall of the female recess may be a transverse base of the female recess. For instance, the female recess may comprise a rearward conical portion which opens in the rearward end of the fixture and a polygonal forward section which communicates with the rearward conical portion at the rearward end thereof and which presents the transverse section at the forward end thereof. An internally threaded bore could extend forwardly into the fixture from the transverse section without adversely affecting the benefit secured by the invention.

The superstructure of the system of the invention may take the form of an abutment for bridging the soft tissue layer overlying the maxilla or mandible.

In an embodiment of the invention at least a section of the outer surface of the fixture is roughened for interlocking with the bone tissue, the at least a section of the outer surface having a rearward edge and a forward edge, and the predetermined position on the outer surface is defined by the rearward edge or a position intermediate the rearward and forward edges. The latter example would be the case where the rearward edge projects from the maxilla or mandible on implantation of the fixture. The roughening may be achieved by macroroughening, e.g. by the provision of screw threads, recesses, holes etc., or by microroughening through blasting, plasma spraying, etching, hydroxyapatite coating, the provision of beads on the outer surface etc. or a mixture of both. The roughening can also be achieved by machining.

The more rearward the attachment level is disposed on the fixture outer surface the more bone tissue is involved in the load carrying. Finite element analysis also indicates that the more rearward the attachment level is disposed on the fixture outer surface the less the peak interfacial shear stress value. A rearwardly disposed attachment level is thus preferable and accordingly in an embodiment of the invention at least a forward section of the fixture which presents the forward end is adapted in use to be inserted into bone tissue for implantation of the fixture, the at least a forward section has a rearward edge and the predetermined position on the fixture outer surface is disposed at the rearward edge of the at least a forward section whereby the predetermined position on the fixture outer surface registers or substantially registers with the outer surface of the maxilla or mandible when the fixture is implanted.

Preferably, the fixture outer surface is adapted to interlock with the bone tissue between the predetermined position on the fixture outer surface and the forward end of the fixture. The predetermined position on the fixture outer surface may coincide with the rearward end of the fixture.

In an embodiment of the invention hereinafter to be described the predetermined interfacing surfaces of the fixture and superstructure are unthreaded surfaces.

In an embodiment of the invention the predetermined interfacing surfaces of the fixture and superstructure interface with one another through direct contact.

In an embodiment of the invention the fixture is an endosteal fixture of root form. By "root form" is meant that the fixture has a generally cylindrical shaft which in use of the fixture is implanted in the bone tissue of the maxilla or mandible. The outer surface of the shaft is roughened for interlocking with the bone tissue, e.g. the shaft may be in the form of a screw. The term "root form" is used to distinguish the fixture from other endosteal fixtures, e.g. the blade form. The various forms of endosteal fixture are shown in Biomaterials Science: An Introduction to Materials in Medicine, Ratner, Buddy D. et al, Chapter 7.4, Academic Press, 1996.

The present invention further provides a fixture for use in a system according to the invention and also a superstructure for use in a system according to the invention.

The invention yet further provides a method of installing a dental restoration in the oral cavity of a patient comprising the steps of providing a fixture having an outer surface at least a section of which is adapted for interlocking with bone tissue of the maxilla or mandible, providing a superstructure on which the dental restoration is formed or mountable, implanting the fixture in the maxilla or mandible of the patient in a forward direction such that at least a forward part of the at least a section of the outer surface thereof is disposed adjacent the bone tissue of the maxilla or mandible, and mounting the superstructure on the fixture such that the superstructure interfaces with the fixture in the forward direction on a surface of the fixture positioned at a level forward of the position at which interlocking between the fixture outer surface and bone tissue commences.

By way of example, embodiments of the present invention will now be described with reference to the accompanying Figures of drawings in which:

DETAILED DESCRIPTION OF THE DRAWINGS

In the Figures of drawings like numerals indicate like parts.

Figure 1:
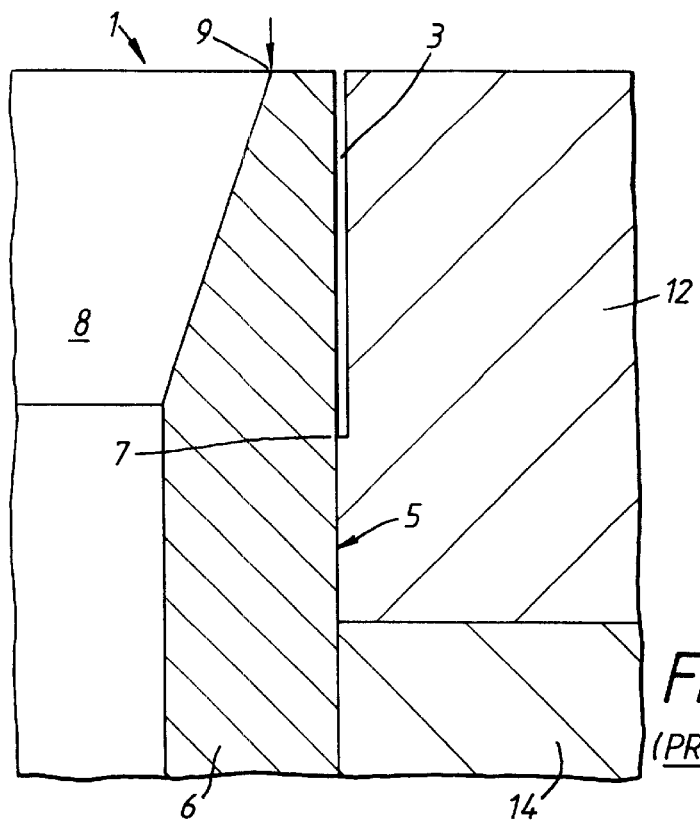
FIG. 1 is a sectional view of a part of a rear end of a fixture of a prior art dental implant system implanted in the bone tissue of a maxilla or mandible in which the outer surface of the fixture comprises a smooth rearward section and an interlocking forward section and to which a superstructure of the system interfaces therewith such that it applies a load to the fixture in the implantation direction through interfacing surfaces disposed rearward of the interlocking forward section of the outer surface.

In FIG. 1 there is shown a sectional view of a part of a rear end of a root form endosteal fixture 1 of a prior dental implant system implanted in the maxilla or mandible with an extent which encompasses both cortical bone tissue 12 and cancellous bone tissue 14. The fixture 1 has a body 6 which presents the outer surface of the fixture 1 which faces the bone tissue 12, 14 and in which a socket 8 extends forwardly from an opening in the rear end of the fixture 1 to a position intermediate the rear end and a forward end of the fixture 1 for use in connecting a superstructure (not shown) such as an abutment to the rear end of the fixture 1.

The outer surface of the fixture 1 is split into a smooth rearward section 3 adjacent the cortical bone 12 and an interlocking screw threaded forward section 5 having an axial extent which encompasses both the cortical and cancellous bone tissue 12, 14. Substantial interlocking between the fixture outer surface and surrounding bone tissue 12, 14 thus starts at a level 7 (the "attachment level") which is disposed at a level below or forward of the entrance point of the fixture 1 into the bone tissue 12, 14.

In this dental implant system the superstructure presents an unthreaded interfacing surface which interfaces with the fixture 1 on an unthreaded edge surface 9 of the socket 8. The implanted fixture 1 is thus loaded in the implantation or forward direction by the superstructure well above or rearward of the attachment level 7, as indicated by the arrow in FIG. 1.

Figure 2:
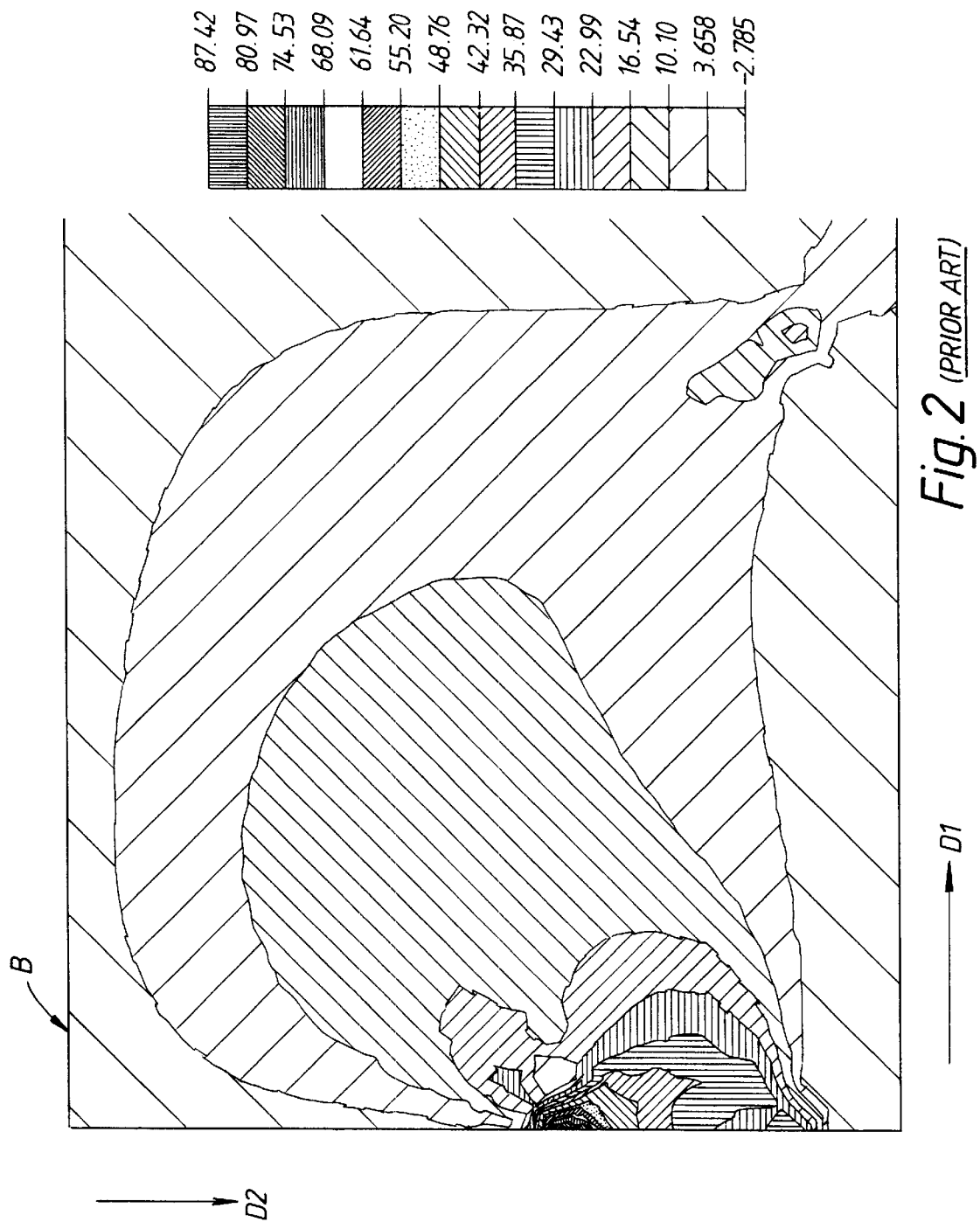
FIG. 2 is a finite element analysis of the stress distribution in the bone tissue adjacent the fixture of FIG. 1 when the superstructure interfaces with the fixture with a load of 1000N being applied to the fixture in the implantation direction through the interfacing surfaces.

FIG. 2 is a finite element analysis of the stress distribution resulting in the bone tissue adjacent the fixture 1 of the dental implant system of FIG. 1 when a forwardly directed load of 1000N is applied to the fixture 1 on the edge surface 9. The x axis in the analysis indicates the distance from the fixture outer surface D1 while the y axis indicates the distance into the bone tissue D2 from the bone tissue surface B. The vertical bar chart on the right hand side is the key for the stresses (MPa) represented in the analysis.

As can be seen from FIG. 2, a relatively high interfacial shear stress peak occurs in the bone tissue of the maxilla or mandible adjacent the fixture 1 at or just below the attachment level 7. The finite element analysis also reveals that a very low stress is experienced in the bone tissue adjacent the smooth rearward outer surface section 3. Consideration of Wolff's law helps to explain why marginal bone resorption is in practice observed around the rearward section 3, namely because the interfacial engagement of the superstructure and the fixture 1 leads to stress conditions in the bone tissue adjacent the smooth rearward outer surface section 3 and the attachment level 7 which are unfavourable for the maintenance of a steady state in the bone tissue.

Figure 3:
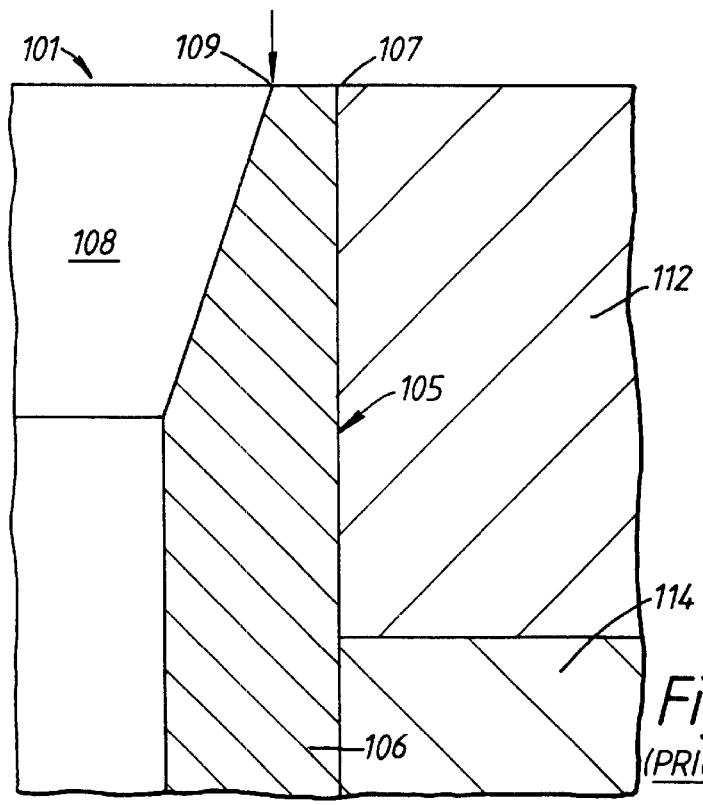
FIG. 3 is a sectional view of a part of a rear end of another fixture of a prior art dental implant system implanted in the bone tissue of a maxilla or mandible having an interlocking outer surface with an attachment level coincident with the fixture entry point into the bone tissue and to which a superstructure of the system interfaces therewith such that it applies a load to the fixture in the implantation direction through interfacing surfaces disposed coincident with the attachment level.

In FIG. 3 there is shown the interfacial loading and bone tissue interlocking conditions for a root form endosteal fixture 101 of another hitherto proposed dental implant system. The fixture 101 is provided with an interlocking machined outer surface 105 with an attachment level 107 which starts where the fixture 101 enters the bone tissue and the superstructure (not shown) has an unthreaded surface which interfaces with an unthreaded edge surface 109 of the socket 108 of the fixture 101 which is at a corresponding level to the attachment level 107. Loading of the fixture 101 in the implantation or forward direction thus also occurs at the level of the attachment level 107.

Figure 4:
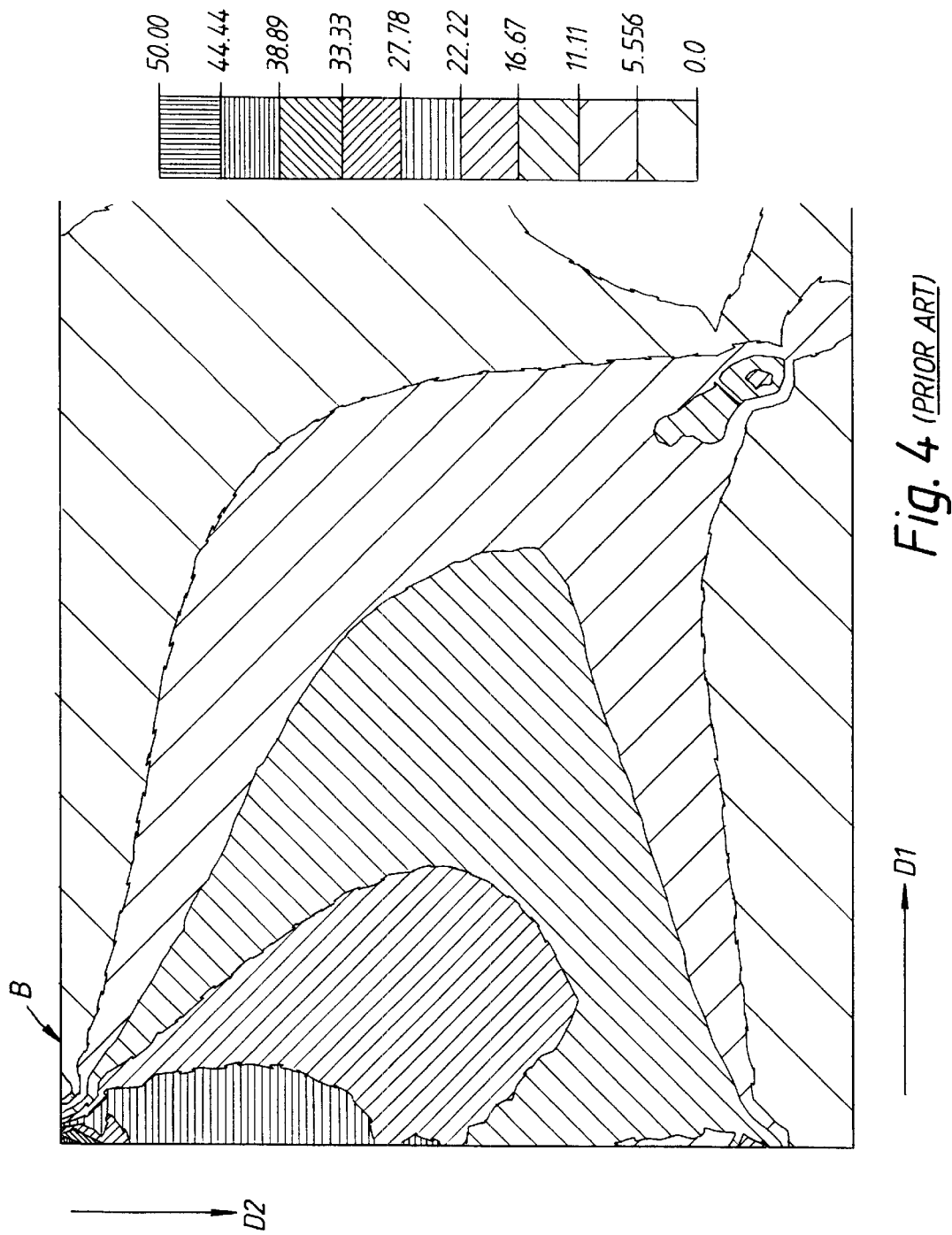
FIG. 4 is a finite element analysis of the stress distribution in the bone tissue adjacent the fixture of FIG. 3 when the superstructure interfaces with the fixture with a load of 1000N being applied to the fixture in the implantation direction through the interfacing surfaces.

A finite element analysis of the stress distribution resulting in the bone tissue adjacent the fixture 101 of the dental implant system of FIG. 3 when a forwardly directed load of 1000N is applied to the fixture 101 on the edge surface 109 is shown in FIG. 4. The maximum interfacial shear stress still coincides with the attachment level 107 although it is reduced as compared to the FIG. 1 system where the attachment level is disposed more forwardly on the fixture outer surface. In addition, all of the coronal cortex is able to support the load of the superstructure in this arrangement. The risk of marginal bone resorption due to disuse hypotrophy is thus reduced for this arrangement.

However, the peak interfacial shear stress is still very high. Moreover, the peak interfacial shear stress in the bone tissue is unfavourably positioned just below the fixture entry point into the bone tissue. This positioning of the peak interfacial shear stress is unfavourable because the entrance point of the fixture 101 into the bone tissue is sensitive due to mild inflammatory processes resulting from surgical trauma.

Figure 5A:
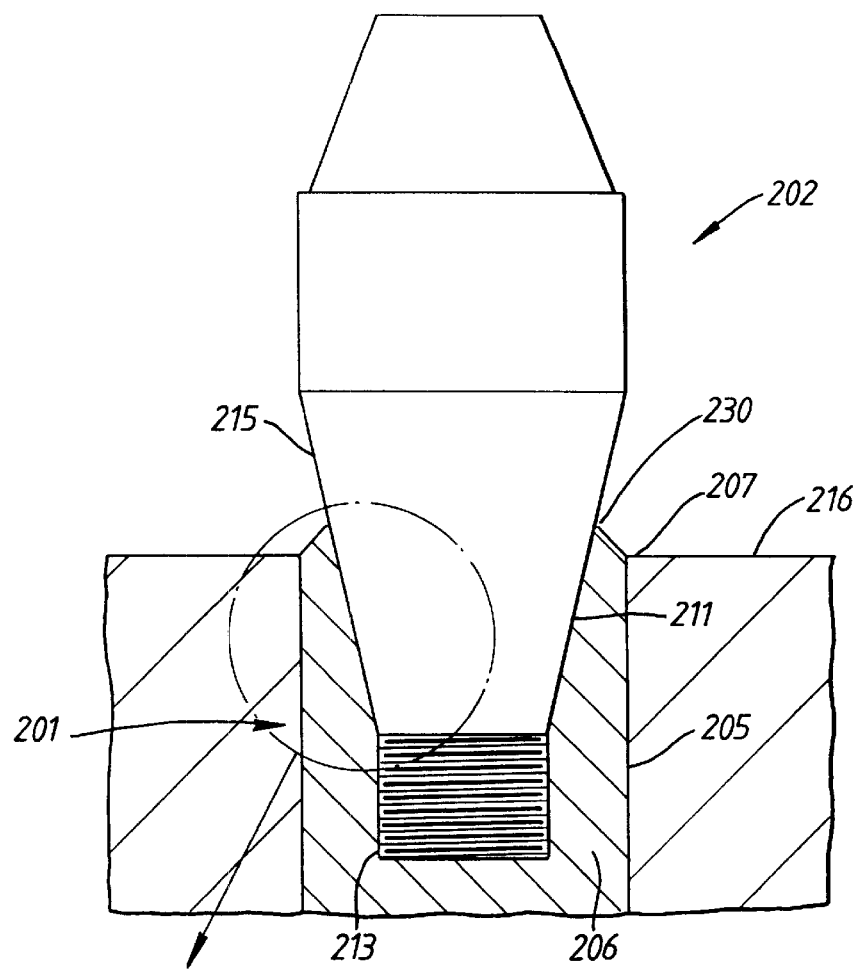
FIG. 5A is a schematic view of a prior art dental implant system comprising a fixture having a rearward end which when the fixture is implanted projects rearward of the outer surface of the bone tissue of the maxilla or mandible and in which there is provided a female recess and further having an interlocking outer surface with an attachment level which starts at the entry point of the fixture in the bone tissue when implanted, and an abutment for bridging the soft tissue layer overlying the maxilla or mandible to support a restoration having a male projection at the forward end thereof which is so constructed and dimensioned vis-a-vis the female recess that the fixture and abutment interface such that the fixture is loaded in the implantation direction through interfacing surfaces which are disposed rearward of the attachment level.
Figure 5B:
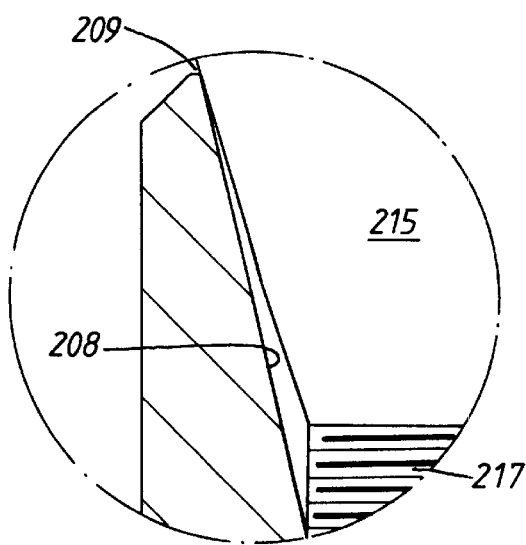
FIG. 5B is an exploded view of the interfacial contact between the fixture and abutment of FIG. 5A.

FIGS. 5A and 5B illustrate a root form endosteal fixture 201 and an abutment 202 of a further prior art dental implant system. The fixture 201 of the system is provided with a socket 208 in a rearward end 230 having a conical unthreaded rearward portion 211 and internally threaded forward portion 213 for a projection at the forward end of the abutment 202 having an unthreaded conical rearward portion 215 and an externally threaded forward portion 217 to interface with for engagement of the abutment 202 to the fixture 201. The fixture 201 is further provided with an interlocking outer surface 205 with an attachment level 207 which starts where the fixture 201 enters the bone tissue.

As shown more clearly in FIG. 5B, the angles of the flank surfaces of the conical rearward portions 211, 215 of the socket and projection are such that the conical rearward portion 215 interfaces with an edge surface 209 of the conical rearward portion 211 at the open end of the socket 208 which is at a level rearward of both the attachment level 207 and the bone tissue outer surface 216. This interfacial engagement in the implantation or forward direction has a "pulling effect" on the abutment 202 when screwed down into the fixture 201. The result of this "pulling effect" is that only rear flank surfaces of the screw thread 217 engage forward flank surfaces of the internal screw thread 213, that is to say, the screw connection imparts a rearwardly directed load to the fixture 201. Thus, loading of the fixture 201 by the abutment 202 in the forward direction only takes place rearward of the attachment level 207.

It is to be noted that the abutment 202 could also be in the form of an abutment assembly comprising a sleeve part having at the forward end thereof the conical portion 215 and a screw part which passes through the sleeve part to present the screw thread forward portion 217. In this case, the screw part has an enlarged head for bearing against a shoulder or the like in the sleeve part when screwed down into the fixture to secure the sleeve part to the fixture. The same "pulling effect" on the screw connection as described above will therefore also result in this case.

Figure 6:
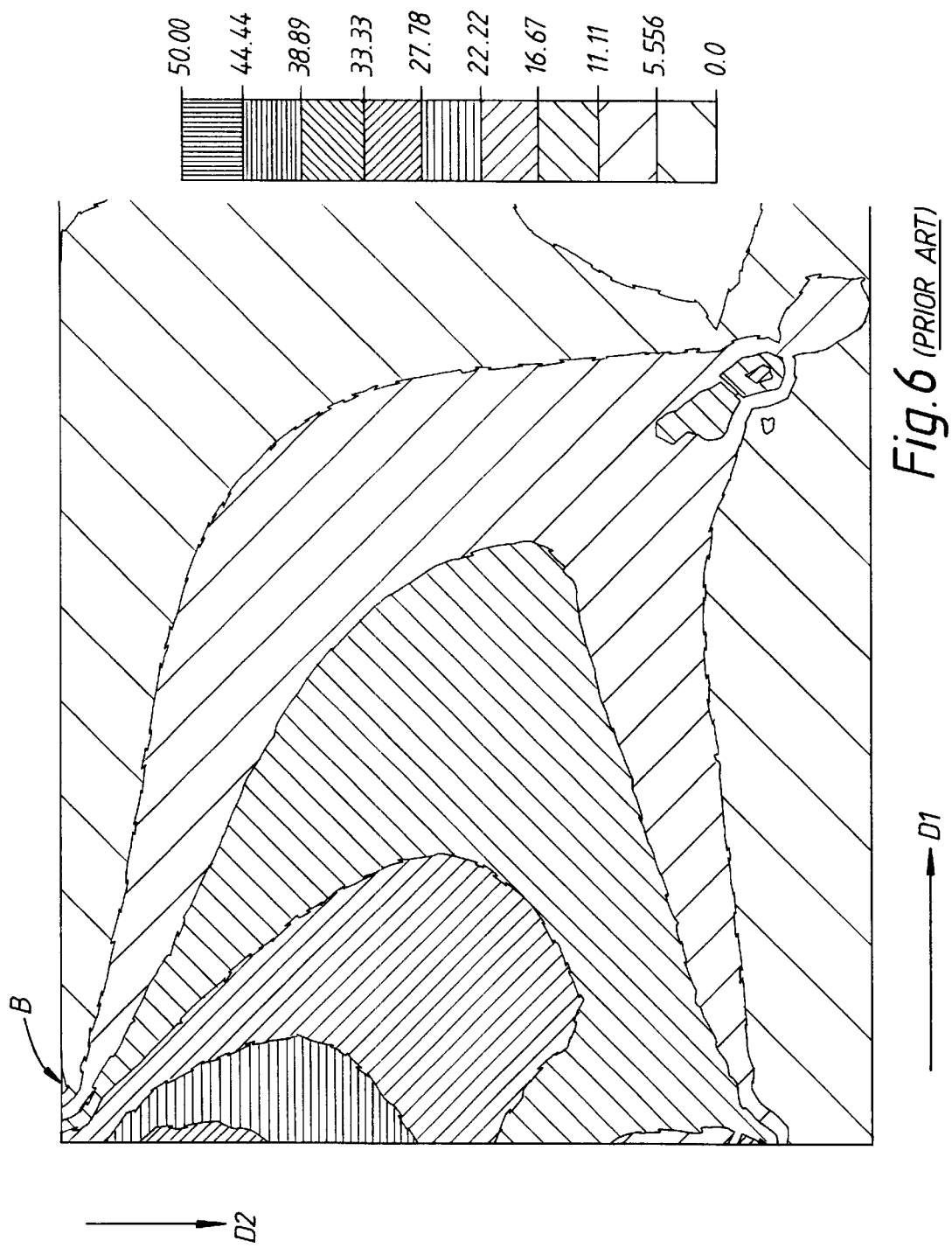
FIG. 6 is a finite element analysis of the stress distribution in the bone tissue adjacent the fixture of FIGS. 5A and 5B when the abutment interfaces with the fixture with a load of 1000N being applied to the fixture in the implantation direction through the interfacing surfaces.

A finite element analysis of the stress distribution resulting in the bone tissue adjacent the fixture 201 of the dental implant system of FIGS. 5A and 5B when a forwardly directed load of 1000N is applied to the fixture 201 on the unthreaded interface surface 209 by the abutment 202 is shown in FIG. 6. The interface of the fixture 201 and abutment 202 in this system results in a reduction of the peak stress in the bone tissue around the fixture 201 under a loading of 1000N and a shifting of the peak interfacial shear stress slightly forwardly of the attachment level 207 as compared to the prior art systems previously described hereinabove with reference to FIGS. 1 to 4. The peak interfacial shear stress is still located proximate the attachment level 207, though, and thus the entrance point of the fixture 201 into the bone tissue.

Figure 7:
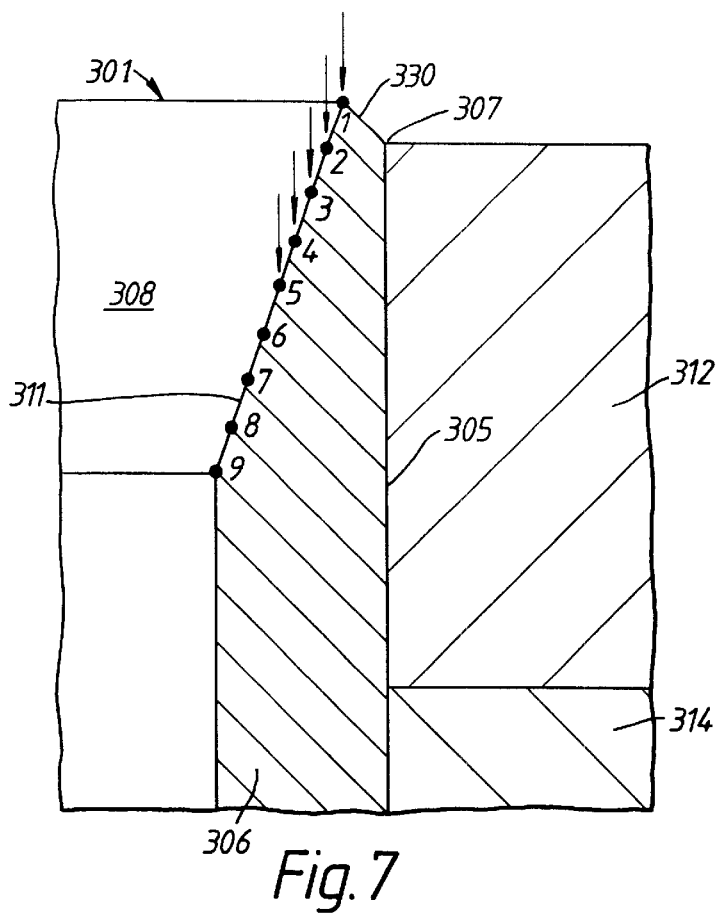
FIG. 7 is a sectional view of a part of a rear end of a fixture of a dental implant system in accordance with the invention implanted in the bone tissue of a maxilla or mandible having an interlocking outer surface with an attachment level coincident with the fixture entry point into the bone tissue and to which a superstructure of the system is adapted to interface such that the fixture is loaded in the implantation direction through interfacing surfaces at a position forward of the attachment level.

In FIG. 7 there is shown a root form endosteal fixture 301 in accordance with the present invention implanted in the bone tissue of the maxilla or mandible. The fixture 301 has an interlocking outer surface 305 with an attachment level 307 which registers with the entry point of the fixture 301 into the bone tissue and a rearward end 330 which projects from the bone tissue and in which there is provided a socket or female recess 308 for a male projection on the forward end of a superstructure such as an abutment (not shown) to engage with. The interlocking capacity of the outer surface is achieved by roughening the is outer surface of the fixture, e.g. by macroroughening, microroughening, machining or a combination of any one of these surface features.

The fixture recess 308 comprises an unthreaded rearward conical portion 311 for an unthreaded conical portion of the superstructure projection to interface with. The flank angles of the conical portions of the recess 308 and projection are such that they are able to at least partially interface whereby all or a part of the forwardly directed load applied to the fixture 301 by the superstructure takes place on one or more of the nodes on the flank surface of the conical portion 311 of the fixture recess 308 disposed forwardly of the attachment level 307.

Figure 8A:
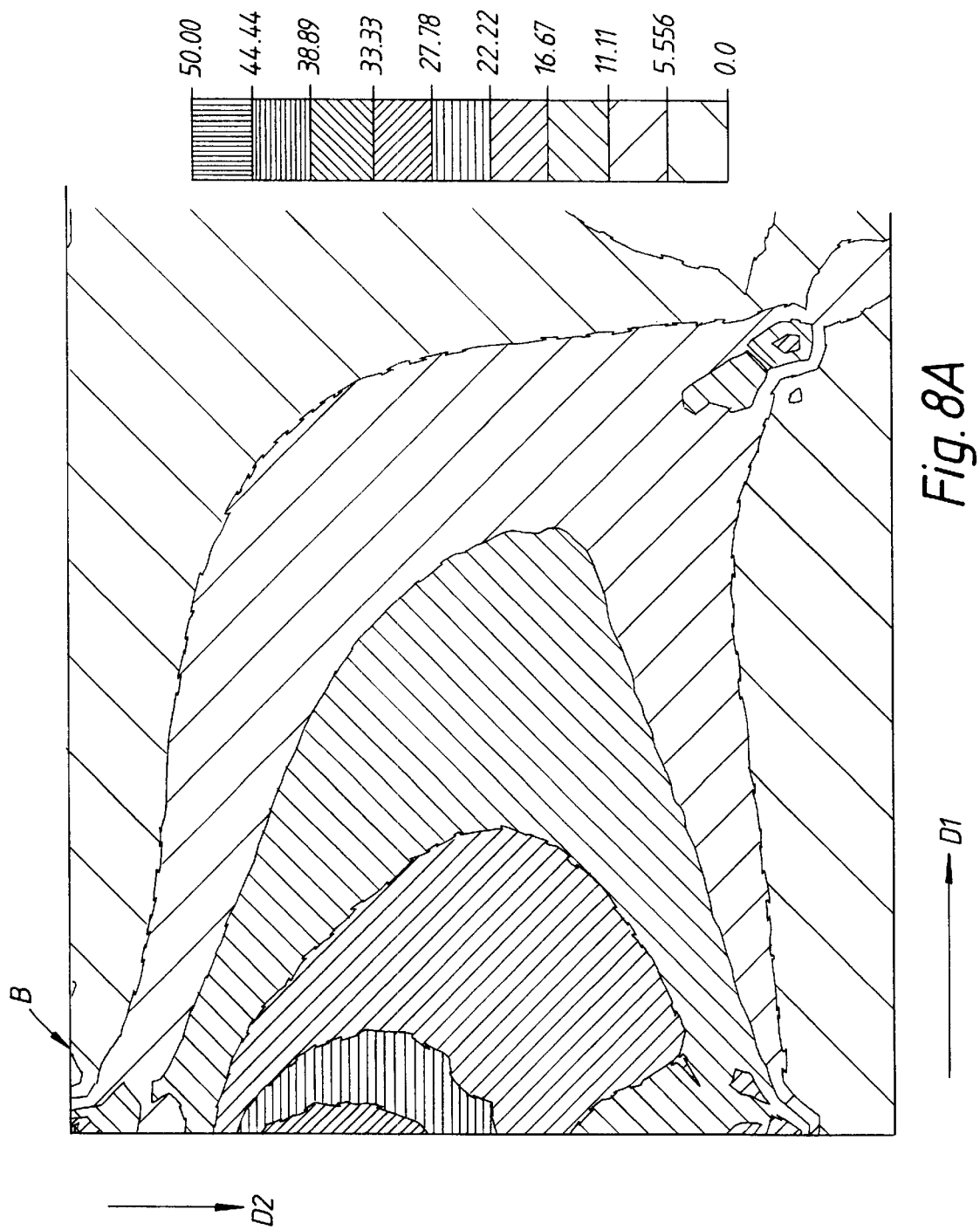
FIGS. 8A to 8C are finite element analyses of the stress distributions in the bone tissue adjacent the fixture of FIG. 7 when a load of 1000N is applied to the fixture by the superstructure in the implantation direction through the interfacing surfaces when disposed at different positions forward of the attachment level or extending across the attachment level.
Figure 8B:
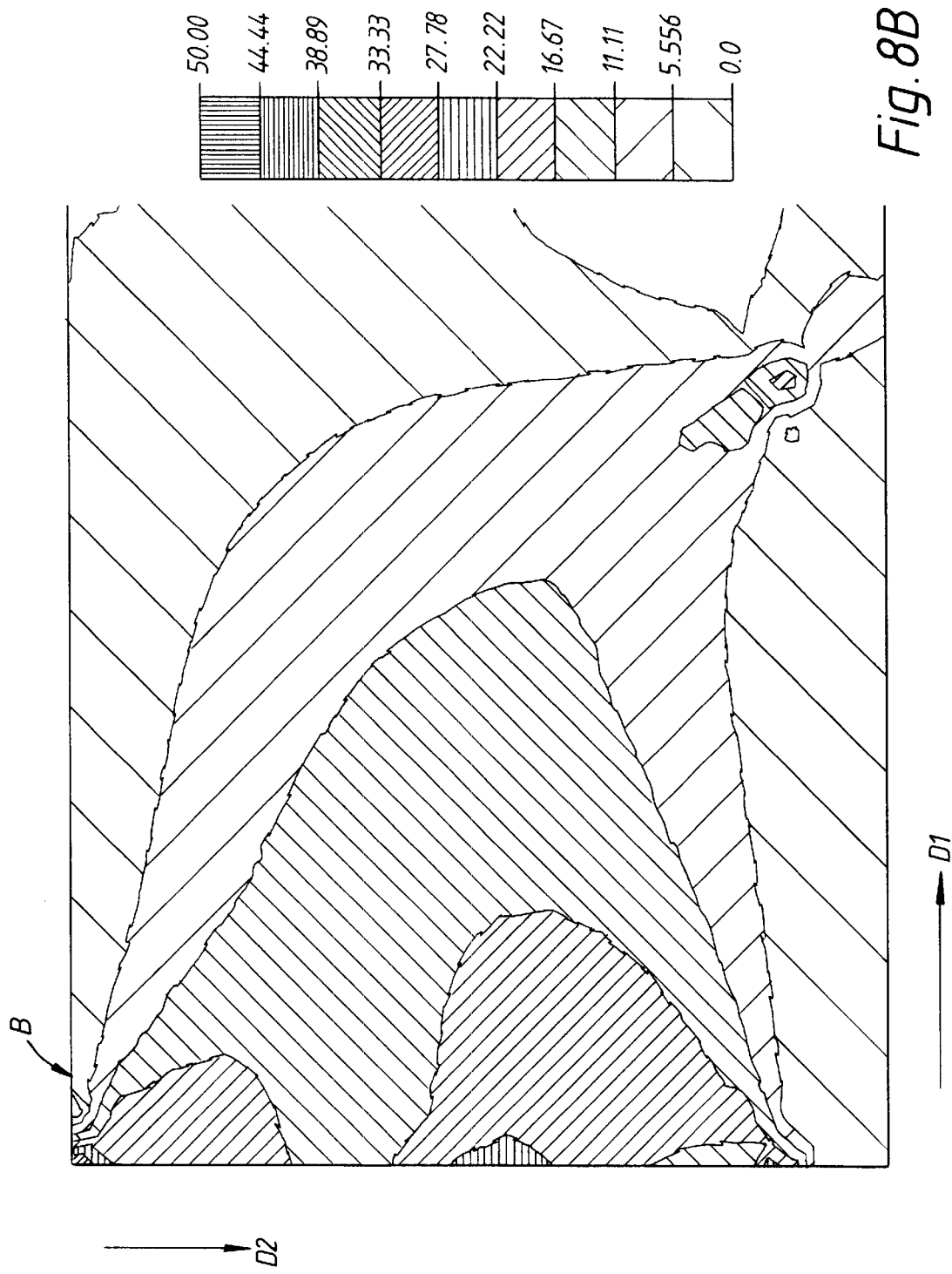
Figure 8C:
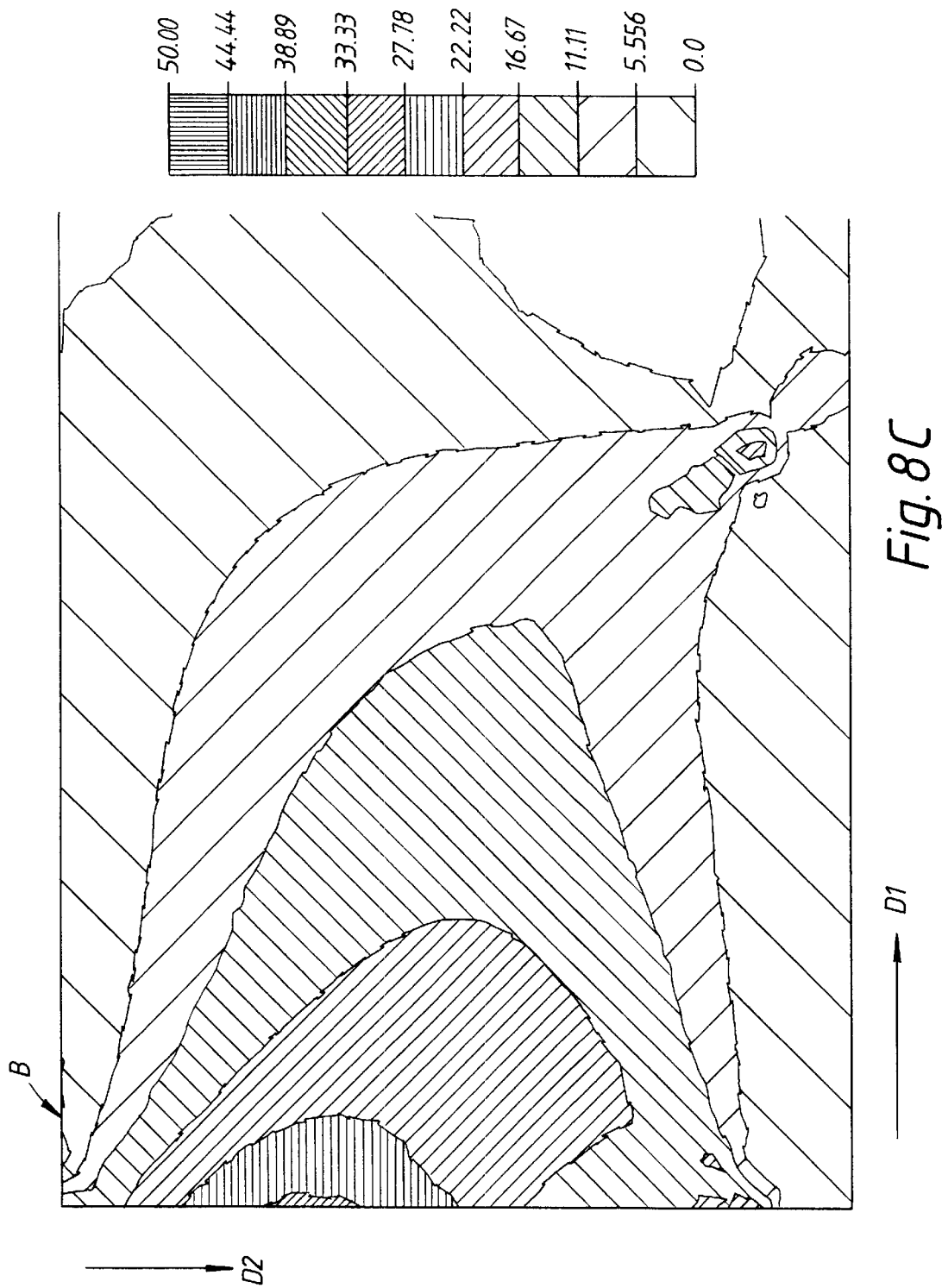

FIGS. 8A to 8C are respectively finite element analyses of the stress distributions in the bone tissue adjacent the implanted fixture 301 of FIG. 7 when the flank surfaces of the conical portions of the fixture recess 308 and superstructure projection are adapted such that:

The superstructure applies a forwardly directed load of 1000N solely upon node 4 on the recess flank surface.
The superstructure applies a forwardly directed load of 1000N solely upon node 7 on the recess flank surface.
The superstructure distributes a forwardly directed load of 1000N over nodes 1 to 5 on the recess flank surface.

The finite element analyses show that by adapting the interfacing ends of the fixture 301 and superstructure so that forwardly directed loading of the fixture 301 by the superstructure takes place through interfacing surfaces disposed forwardly of the attachment level 307 results in the peak interfacial shear stress in the bone tissue adjacent the fixture 301 being disposed progressively further forwardly of the attachment level 307 and also to be generally reduced in value as compared to the prior art systems.

Figure 9B:
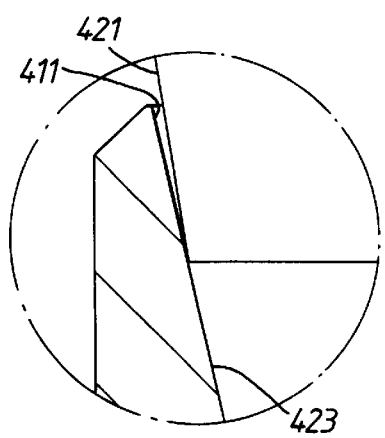
FIG. 9B is an exploded view of the interfacial contact between the fixture and abutment of FIG. 9A.
Figure 9A:
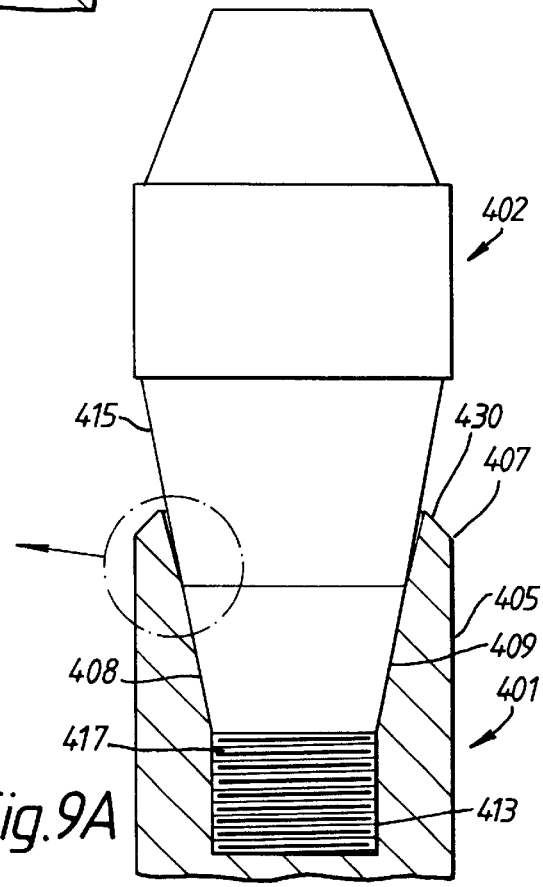
FIG. 9A is a schematic view of a dental implant system in accordance with the invention comprising a fixture having a rearward end which when the fixture is implanted projects rearward of the outer surface of the bone tissue of the maxilla or mandible and in which there is provided a female recess and further having an interlocking outer surface with an attachment level which starts at the entry point of the fixture in the bone tissue when implanted, and an abutment for bridging the soft tissue layer overlying the maxilla or mandible to support a restoration having a male projection at the forward end thereof which is so constructed and dimensioned vis-à-vis the female recess that the fixture and abutment interface such that the fixture is loaded in the implantation direction through interfacing surfaces which are disposed at a position forward of the attachment level.

As an example of how the interfacial contact described hereinabove with reference to FIGS. 7 and 8A–8C can be achieved, FIGS. 9A and 9B show a root form endosteal fixture 401 and an abutment 402 of a system in accordance with the invention having interfacing surfaces which interface at a level forward of a rearward edge 407 of the interlocking section 405 of the outer surface which post-implantation will register with the entry point of the fixture 401 in the bone tissue. The interlocking capacity of the outer surface is achieved by roughening the outer surface of the fixture, e.g. by macroroughening, microroughening, machining or a combination of any one of these surface features.

The fixture 401 presents a rearward end 430 which will project from the bone tissue when implanted and in which a socket 408 having an unthreaded rearward conical portion 411 is provided. The abutment 402 has a male projection at the forward end thereof with an unthreaded rearward conical portion 415 for interfacing with the socket 408 in the fixture 401. The flank surface of the conical portion 415 of the abutment projection is broken into two sections 421, 423 of slightly differing angles so that the interfacial contact of the abutment 402 and fixture 401 in the implantation or forward direction occurs between the section 423 of the abutment projection and a section 409 of the conical portion 411 of the socket 408 forward of the rearward edge or attachment level 407. Essential transmittance of the forwardly directed load will thus take place at a level forward of the rearward edge or attachment level 407 due to the essential interfacial contact between the abutment 402 and the fixture 401 being located further forward in the conical portion 411 of the socket 408 in the fixture 401. Interfacial contact takes place in the range of 0.1–5 mm forward of the rearward edge or attachment level 407.

It will be appreciated that the angle of the flank surface of the conical portion 411 of the fixture socket 408 could also be broken to allow favourable interfacial contact between surfaces of the fixture 401 and the abutment 402 forward of the rearward edge or attachment level 407.

A soft buffer material such as silicone rubber could be placed in the annular space between the rearward section 421 of the rearward conical portion 415 of the male projection of the abutment 402 and the conical portion 411 of the socket 408 in the fixture 401 to support the abutment 402 without providing a medium for an appreciable forwardly directed load to be transmitted to the fixture 401. As examples, there can be mentioned use of an ultra thin soft polymer O-ring or a painted layer on the conical portion 411 of the socket 408.

If the flank angle of the conical portion 415 of the abutment projection is made equal to or substantially equal to the flank angle of the conical portion 411 of the socket 408 in the fixture 401 a forwardly directed load will be distributed across the attachment level 407 due to the conical portions 411, 415 of the socket 408 and male projection interfacing across the attachment level 407.

For both cases a reduced interfacial shear stress peak and more favourable stress distribution in the bone tissue adjacent the fixture 401 will result by virtue of the fixture 401 being loaded in the forward direction on surfaces forward of the attachment level 407.

Figure 10:
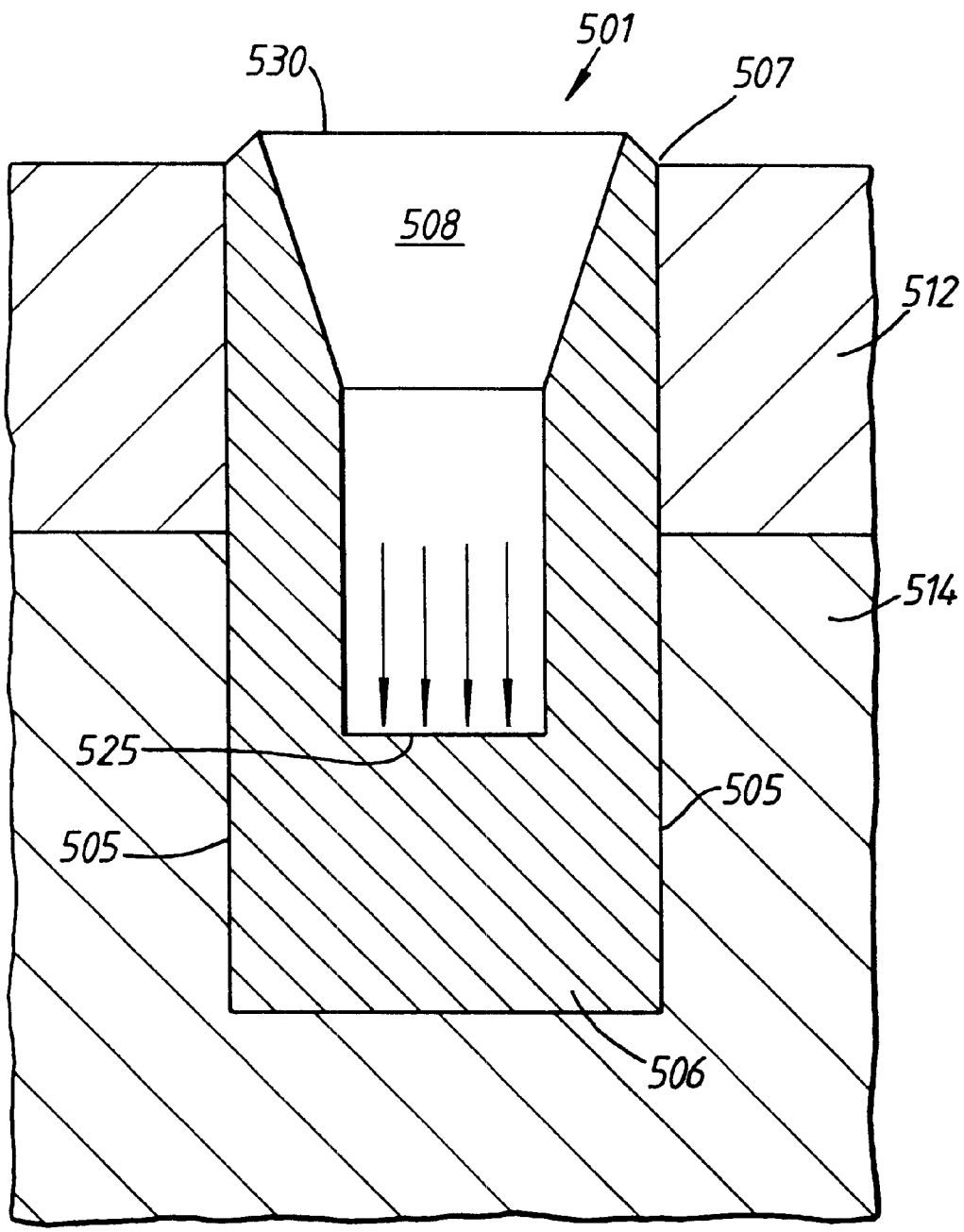
FIG. 10 is a sectional view of another fixture of a dental implant system in accordance with the invention implanted in the bone tissue of a maxilla or mandible having an interlocking outer surface with an attachment level coincident with the fixture entry point into the bone tissue and to which a superstructure of the system is able to interface therewith such that the fixture is loaded in the implantation direction through interfacing surfaces disposed forward of the attachment level.

Turning now to FIG. 10, there is shown another root form endosteal fixture 501 in accordance with the invention having an interlocking outer surface 505 with an attachment level 507 coincident with the bone tissue surface when implanted and a rear end 530 which when the fixture is implanted projects rearwardly from the bone tissue and in which there is provided a socket 508 for a projection on a superstructure such as an abutment (not shown) to seat in. Again, the interlocking capacity of the outer surface is achieved by roughening the outer surface of the fixture, e.g. by macroroughening, microroughening, machining or a combination of any one of these surface features.

In this case the socket 508 in the fixture 501 and the abutment projection are adapted such that interfacial contact between the fixture 501 and superstructure in the forward direction only takes place on a base surface 525 of the socket 508 which as can be seen is disposed forwardly of the attachment level 507. Axial loading of the fixture in the forward direction thus only takes places forwardly of the attachment level 507. The base surface 525 is in the range of 0.1 mm to about 10 mm forward of the attachment level 507 with more improved stress conditions being obtained as one progresses further towards the upper limit of this range.

Figure 11:
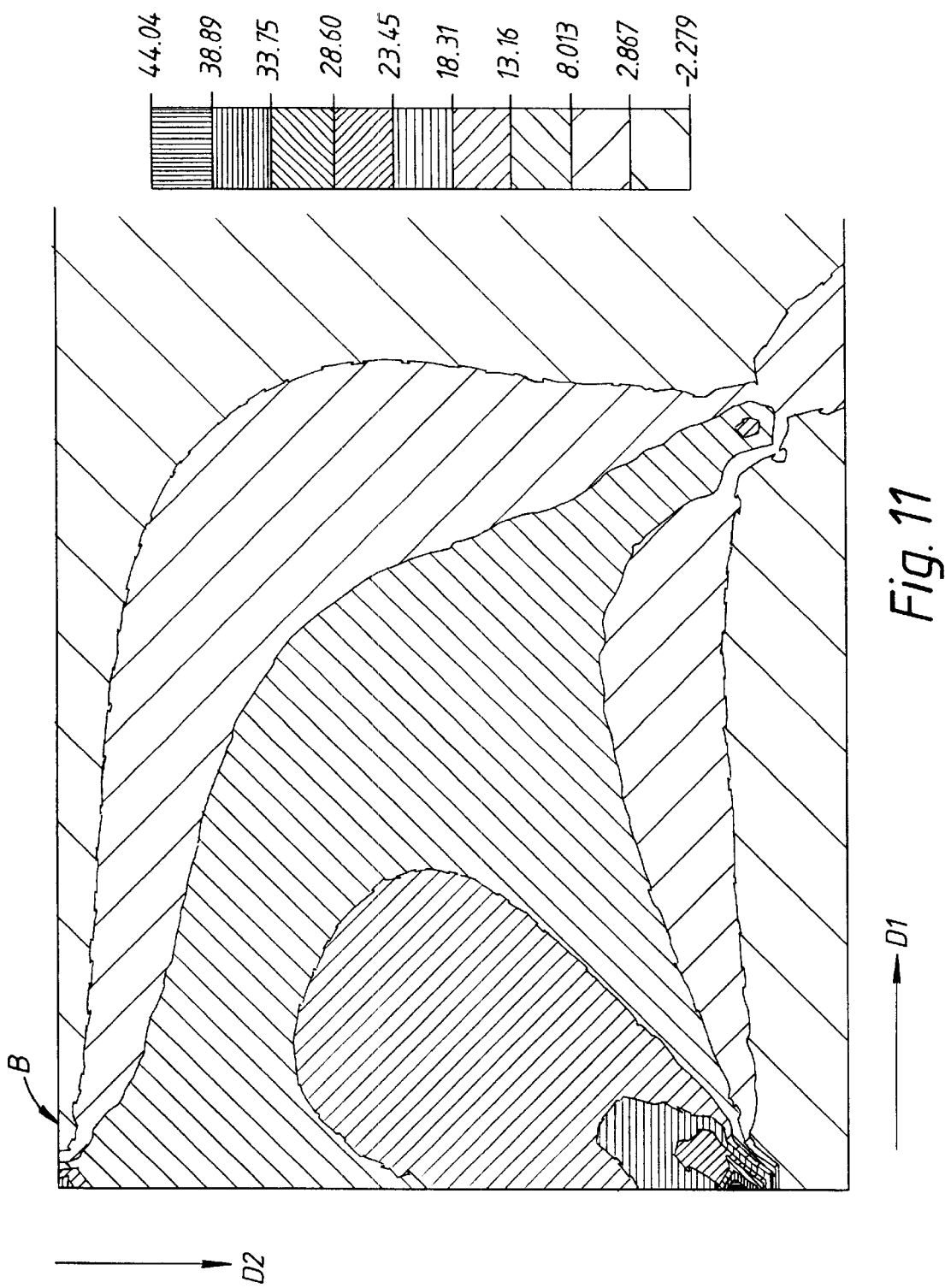
FIG. 11 is a finite element analysis of the stress distribution in the bone tissue adjacent the fixture of FIG. 10 when the superstructure interfaces with the fixture with a load of 1000N being applied to the fixture in the implantation direction through the interfacing surfaces.

FIG. 11 is a finite element analysis of the stress distribution in the bone tissue adjacent the implanted fixture 501 of FIG. 10 when a forwardly directed load of 1000N is applied to the base surface 525 of the socket 508 by the superstructure. This shows that the stresses in the bone tissue adjacent the fixture 501 are again favourably distributed due to the forwardly directed load being applied below the attachment level 507. The same result would also be observed where this interfacial contact was maintained with a screw threaded projection at the forward end of the superstructure screwing into an internally threaded bore extending forwardly into the fixture 501 from the base surface 525.

It will be appreciated that it may be the case that a rearward section of the interlocking outer surface of a fixture will project from the maxilla or mandible. In such a case the attachment level will be disposed at the fixture entry point into the maxilla or mandible in-between the rearward and forward ends of the interlocking outer surface when the fixture is implanted. In accordance with the invention, axial loading of the fixture by the superstructure in the implantation or forward direction will take place through interfacing surfaces forward of said position between the rearward and forward ends of the interlocking outer surface.

It will further be appreciated by those versed in the art that the components of the system of the invention can be made from conventional materials of the art, e.g. commercially pure titanium, and by conventional methods.

In summary, the present invention provides a dental implant system comprising a fixture having an interlocking outer surface and a superstructure interfaceable with the fixture in which the stress distribution around the fixture when implanted is enhanced by adapting the interfacial contact between the fixture and superstructure such that the superstructure applies a forwardly directed load to the fixture through interfacing surfaces at a position which is disposed at a level forward of the attachment level of the interlocking outer surface of the fixture.

I claim:

1. A dental implant system comprising:
   (a) a fixture (301;401;501) capable of being implanted in bone tissue (312, 314; 512, 514) of the maxilla or mandible by displacement of the fixture in a forward direction in the maxilla or mandible, the fixture comprising:
   a forward end,
   a rearward end providing a female recess having a rearward opening and a boundary wall (330; 430; 530), and
   an outer surface (305; 405; 505) which extends between the forward and rearward ends and which forwardly of a predetermined position (307; 407; 507) on the outer surface is adapted for interlocking with bone tissue of the maxilla or mandible,
   said boundary wall of the female recess extending forwardly from said recess opening and beyond said predetermined position; and
   (b) a superstructure (402) capable of being securely mounted on the fixture, the superstructure comprising:
   a forward end providing a male projection having a boundary wall
   wherein,
   (i) said boundary wall of the female recess of the fixture and said boundary wall of the projection of the superstructure each present a predetermined interfacing surface capable of interfacing with each other, each of said interfacing surfaces being disposed forwardly of the predetermined position, and each of said interfacing surfaces being presented by a predetermined forward section of the respective boundary wall and having a substantially conical profile with flank surfaces which converge in the forward direction at a substantially common angle, and
   (ii) the boundary wall of the projection of the superstructure and the boundary wall of the female recess of the fixture are sized and configured to be spaced-apart from each other rearward from where the predetermined forward sections interface.

2. A system according to claim 1, wherein the predetermined interfacing surfaces of the fixture and the superstructure are the only interfacing surfaces of the fixture and superstructure which are adapted to interface in the forward direction with one another.

3. A system according to claim 1 or 2, wherein the predetermined interfacing surfaces of the fixture and superstructure are sized and configured to interface at a level which is in the range of 1 mm up to approximately 10 mm forward of the predetermined position on the fixture outer surface.

4. A system according to 1 or 2, wherein the predetermined interfacing surfaces of the fixture and superstructure are sized and configured to interface at a level which is approximately 0.1–1 mm forward of the predetermined position on the fixture outer surface.

5. A system according to claim 1, wherein the extent of the predetermined forward section of the boundary wall of the female recess in the forward direction is greater than the extent of the predetermined rearward section of the boundary wall of the female recess in the forward direction.

6. A system according to claim 1, wherein the section of the boundary wall of the female recess rearward of the predetermined interfacing surface of the boundary wall of the female recess is of a conical profile with flank surfaces which converge in the forward direction.

7. A system according to claim 6, wherein the flank surfaces of the rearward section of the boundary wall of the female recess converge in the forward direction at the common angle.

8. A system according to claim 7, wherein the rearward section of the male projection is of a conical profile with flank surfaces which converge in the forward direction at an angle which is more acute relative to the forward direction than the common angle.

9. A system according to claim 8, wherein the predetermined surfaces of the boundary walls of the female recess and male projection have a substantially conical profile with flank surfaces which converge in the forward direction at a common angle or substantially common angle.

10. A system according to claim 6, wherein the rearward section of the male projection is of a conical profile with flank surfaces which converge in the forward direction at an angle which is more acute relative to the forward direction than the common angle.

11. A system according to claim 1, wherein the rearward section of the boundary wall of the female recess extends rearwardly to the rearward end of the fixture.

12. A system according to claim 1, wherein the predetermined surface of the boundary wall of the female recess is presented by a transverse section (525) of the boundary wall.

13. A system according to claim 12, wherein the transverse section of the boundary wall of the female recess is a transverse base of the female recess.

14. A system according to claim 13, wherein the female recess comprises a rearward conical portion which opens in the rearward end of the fixture and a polygonal forward section which communicates with the rearward conical portion at the rearward end thereof and which presents the transverse section at the forward end thereof.

15. A system according to claim 12, wherein the female recess comprises a rearward conical portion which opens in the rearward end of the fixture and a polygonal forward section which communicates with the rearward conical portion at the rearward end thereof and which presents the transverse section at the forward end thereof.

16. A system according to claim 1, wherein the superstructure takes the form of an abutment (402) for bridging the soft tissue layer overlying the maxilla or mandible.

17. A system according to claim 1, wherein at least a section of the outer surface of the fixture (305; 405; 505) is roughened for interlocking with the bone tissue, that the at least a section of the outer surface has a rearward edge and a forward edge and that the predetermined position on the outer surface is defined by the rearward edge or a position intermediate the rearward and forward edges.

18. A system according to claim 17, wherein at least a section of the fixture outer surface is macroroughened.

19. A system according to claim 17 or 18, wherein at least a section of the fixture outer surface is microroughened.

20. A system according to claim 17, wherein at least a section of the fixture outer surface is roughened by machining thereof.

21. A system according to claim 1, wherein at least a forward section of the fixture which presents the forward end is adapted in use to be inserted into bone tissue for implantation of the fixture, that at least a forward section has a rearward edge and that the predetermined position on the fixture outer surface is disposed at the rearward edge of the at least a forward section whereby the predetermined position on the fixture outer surface registers or substantially registers with the outer surface of the maxilla or mandible when the fixture is implanted.

22. A system according to claim 1, wherein all or substantially all of the fixture outer surface is adapted to interlock with the bone tissue between the predetermined position on the fixture outer surface and the forward end of the fixture.

23. A system according to claim 1, wherein the predetermined position on the fixture outer surface coincides with the rearward end of the fixture.

24. A system according to claim 1, wherein the predetermined interfacing surfaces of the fixture and superstructure are unthreaded surfaces.

25. A system according to claim 1, wherein the predetermined interfacing surfaces of the fixtures and superstructure interface with one another through direct contact.

26. The dental implant system according to claim 1, wherein
a section of the boundary wall of the recess of the fixture disposed forward of the interfacing surface of the boundary wall of the recess is screw-threaded,
the superstructure is integrally formed with an externally screw-threaded projection disposed forward of the interfacing surface of the boundary wall of the superstructure, and
the screw-threaded section of the recess and the screw-threaded projection are sized and configured to screw engage each other so that the interfacing surfaces are brought into contact.

27. The dental implant system according to claim 1, wherein
the outer surface of the fixture is adapted for interlocking with bone tissue of the maxilla or mandible by comprising screw threads capable of screw insertion with bone tissue of the maxilla or mandible.

28. A method of installing a dental restoration in the oral cavity of a patient comprising the steps of:
providing a fixture (301; 401; 501) having an outer surface, wherein at least a section of the outer surface (305; 405; 505) is adapted for interlocking with bone tissue (312; 314; 512; 514) of the maxilla or mandible, and a rearward end providing a female recess having a rearward opening and a boundary wall,
providing a superstructure (402) on which the detail restoration is formed or mountable, the superstructure comprising a forward end providing a male projection having a boundary wall, wherein
said boundary wall of the female recess of the fixture and said boundary wall of the projection of the superstructure each present a predetermined interfacing surface capable of interfacing with each other, each of said interfacing surfaces being presented by a predetermined forward section of the respective boundary wall and having a substantially conical profile with flank surfaces which converge in the forward direction at a substantially common angle,
implanting the fixture in the maxilla or mandible of the patient in a forward direction in the maxilla or mandible such that at least a forward part of at least a section of the outer surface of the fixture is positioned at a level forward of a predetermined position at which interlocking between the fixture outer surface and bone tissue commences, and said boundary wall of the female recess extends forwardly from said recess opening and beyond said predetermined position, and
mounting the superstructure on the fixture such that the predetermined interfacing surfaces of the superstructure and the fixture, respectively, interface, each of said interfacing surfaces being disposed forwardly of the predetermined position, and the boundary wall of the projection of the superstructure and the boundary wall of the female recess of the fixture are spaced-apart from each other rearward from where the predetermined forward sections interface.

29. A method according to claim 28, further comprising the step of implanting the fixture such that at least a section of the fixture outer surface is disposed adjacent to bone tissue of the maxilla or mandible.

30. A method according to claim 28 or 29, further comprising the steps of implanting the fixture such that interlocking between bone tissue of the maxilla or mandible and the fixture outer surface commences at the surface of the maxilla or mandible and mounting the superstructure on the fixture such that the superstructure and fixture interface in the forward direction through surfaces thereof are positioned at a level forward of the surface of the maxilla or mandible.

31. A fixture (301; 401; 501) of a dental implant system capable of being implanted in bone tissue (312, 314; 512, 514) of the maxilla or mandible by displacement of the fixture in a forward direction in the maxilla or mandible, the fixture comprising:

a forward end, a rearward end providing a female recess having a rearward opening and a boundary wall (330; 430; 530), and an outer surface (305; 405; 505) which extends between the forward and rearward ends and which forwardly of a predetermined position (307; 407; 507) on the outer surface is adapted for interlocking with bone tissue of the maxilla or mandible;

said boundary wall of the female recess extending forwardly from said recess opening and beyond said predetermined position, wherein the fixture is further adapted for securably mounting a superstructure thereon, the superstructure comprising:

a forward end providing a male projection having a boundary wall wherein, (i) said boundary wall of the female recess of the fixture and said boundary wall of the projection of the superstructure each present a predetermined interfacing surface capable of interfacing with each other, each of said interfacing surfaces being disposed forwardly of the predetermined position, and each of said interfacing surfaces being presented by a predetermined forward section of the respective boundary wall and having a substantially conical profile with flank surfaces which converge in the forward direction at a substantially common angle, and (ii) the boundary wall of the projection of the superstructure and the boundary wall of the female recess of the fixture are sized and configured to be spaced-apart from each other rearward from where the predetermined forward sections interface.

32. The fixture according to claim 31, wherein a section of the boundary wall of the recess of the fixture disposed forward of the interfacing surface of the boundary wall of the recess is screw-threaded enabling screw engagement with an externally screw-threaded projection integrally formed with the superstructure.

33. A superstructure of a dental implant system capable of being securably mounted on a dental implant system fixture (301; 401; 501), the fixture capable of being securably implanted in bone tissue (312, 314; 512, 514) of the maxilla or mandible by displacement of the fixture in a forward direction in the maxilla or mandible, and the fixture comprising:

a forward end, a rearward end providing a female recess having a rearward opening and a boundary wall (330; 430; 530), and an outer surface (305; 405; 505) which extends between the forward and rearward ends and which forwardly of a predetermined position (307; 407; 507) on the outer surface is adapted for interlocking with bone tissue of the maxilla or mandible;

said boundary wall of the female recess extending forwardly from said recess and beyond said predetermined position, the superstructure comprising:

a forward end providing a male projection having a boundary wall, wherein, (i) said boundary wall of the female recess of the fixture and said boundary wall of the projection of the superstructure each present a predetermined interfacing surface capable of interfacing with each other, each of said interfacing surfaces being disposed forwardly of the predetermined position, and each of said interfacing surfaces being presented by a predetermined forward section of the respective boundary wall and having a substantially conical profile with flank surfaces which converge in the forward direction at a substantially common angle, and (ii) the boundary wall of the projection of the superstructure and the boundary wall of the female recess of the fixture are sized and configured to be spaced-apart from each other rearward from where the predetermined forward sections interface.

34. The superstructure according to claim 33 in which the superstructure is an abutment (402) for bridging the soft tissue layer which overlies the maxilla or mandible.

35. The superstructure according to claim 33, wherein the superstructure is integrally formed with an externally screw-threaded projection disposed forward of the interfacing surface of the boundary wall of the superstructure enabling screw engagement with the fixture.

* * * * *